US00PP26085P3

(12) United States Plant Patent

Nixon et al.

(10) Patent No.: US PP26,085 P3

(45) Date of Patent: Nov. 17, 2015

(54) APRICOT TREE NAMED 'STB14/22'

(50) Latin Name: *Prunus armeniaca*
Varietal Denomination: StB14/22

(71) Applicant: The New Zealand Institute for Plant and Food Research Limited, Auckland (NZ)

(72) Inventors: Arlene E. Nixon, Alexandra (NZ); Michael T. Malone, Havelock North (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 189 days.

(21) Appl. No.: 13/987,023

(22) Filed: Jun. 26, 2013

(65) Prior Publication Data

US 2013/0347152 P1 Dec. 26, 2013

Related U.S. Application Data

(60) Provisional application No. 61/664,159, filed on Jun. 26, 2012.

(51) Int. Cl.
*A01H 5/08* (2006.01)
*A01H 5/00* (2006.01)

(52) U.S. Cl.
USPC ..... Plt./186
CPC ..... *A01H 5/00* (2013.01)

(58) Field of Classification Search
USPC ..... Plt./186
See application file for complete search history.

*Primary Examiner* — Susan McCormick Ewoldt
(74) *Attorney, Agent, or Firm* — Lathrop & Gage LLP

(57) ABSTRACT

A new and distinct apricot variety is described. The variety results from selection among a population of seedlings derived from controlled crossing of the apricot varieties known as 'Late Moorpark' (not patented) and 'Bhart' (not patented), marketed as Orangered™. The new variety is distinguished from others by the deep red over color of the mature fruit accompanied by mid-orange colored firm flesh with high soluble solids content. Fruit of 'StB14/22' matures in mid-February in Otago, New Zealand.

5 Drawing Sheets

Genus and species of plant claimed: *Prunus armeniaca.*
Variety denomination: 'StB14/22'.

BACKGROUND TO THE INVENTION

Seedlings obtained from the deliberate crossing of the apricot varieties 'Bhart' (not patented) (female parent), marketed as Orangered™, and 'Late Moorpark' (not patented) (male parent), in September 2001, were planted out at Clyde, Otago, New Zealand, where the cross was also conducted. In February 2006, 'StB14/22' was identified as having potential as a new variety. Later in 2006, 'StB14/22' was asexually propagated from bud wood taken at Clyde and budded at Hawkes Bay, New Zealand, onto 'Golden Queen' (not patented) peach seedlings, the standard apricot rootstock in New Zealand. The resulting trees were planted out at Clyde in the Southern Hemisphere winter of 2007, and were subsequently found to be true to type demonstrating that the characteristics of the new variety, 'StB14/22', are stable and transmitted without change through succeeding generations.

SUMMARY OF THE INVENTION

'StB14/22' is characterised by medium sized fruit (70-100 g) with a deep red overcolor, mid orange colored firm flesh and high soluble solids content which mature in mid-late February in Otago, New Zealand. 'StB14/22' is distinguished from a number of varieties by the following characteristics:

'StB14/22' has firmer flesh, higher acidity, and a slightly later harvest date when compared to 'F168' (U.S. Plant Pat. No. 16,071) (also known as 'Larclyd', marketed as Genevieve) grown at Clyde.

StB14/22 is harvested more than a month later than Bhart. At Clyde, StB14/22 is harvested in mid-February and 'Bhart' in early January.

Fruit of 'StB14/22' is elliptical in shape where as 'F194' (U.S. Plant Pat. No. 16,119) (also known as 'Southern Cross') is round, as is that of 'Late Moorpark'.

BRIEF DESCRIPTION OF THE DRAWINGS

The accompanying photographs show typical specimens of the plant, fruit, and leaves of the new variety as depicted in colors as nearly true as is reasonably possible to make the same in color illustrations of this character.

DETAILED DESCRIPTION

Figure 1:
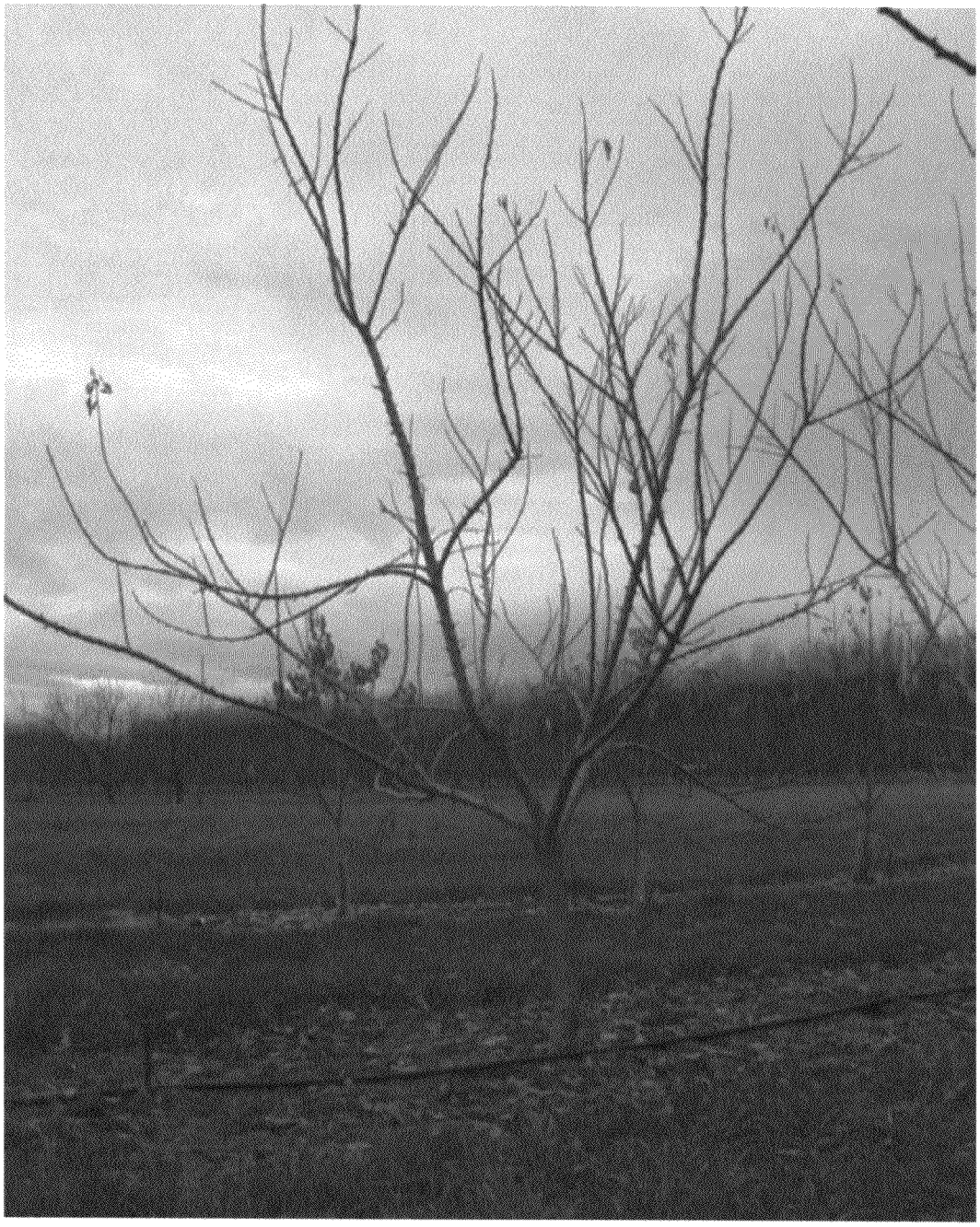
FIG. 1 shows a young 'StB14/22' tree, approximately three years old, in winter.
Figure 2:
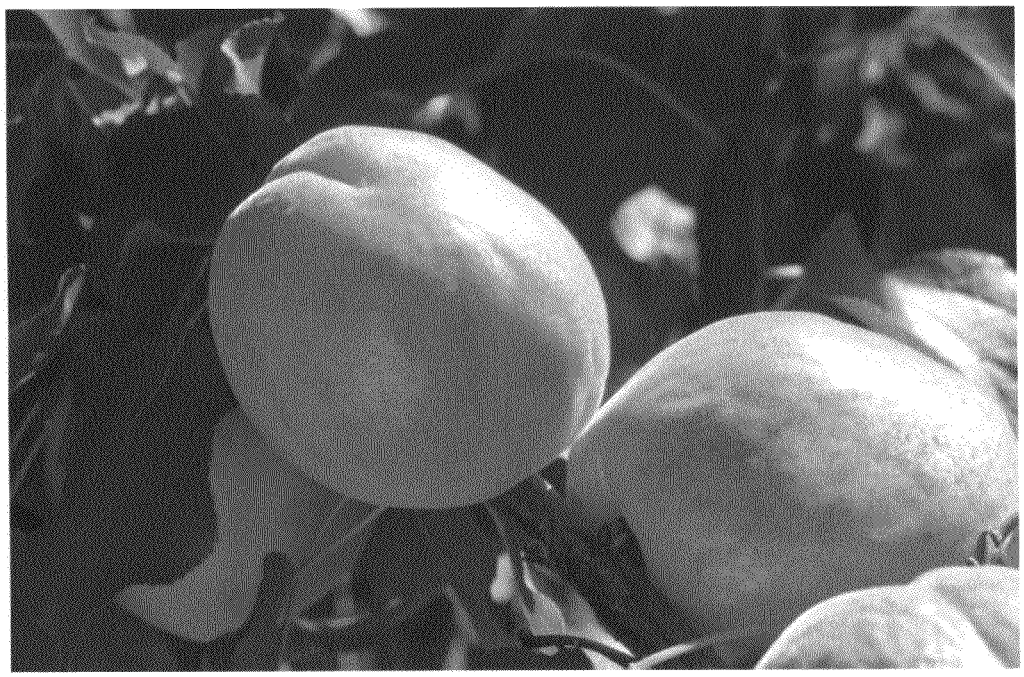
FIG. 2 shows a 'StB14/22' fruit on the tree.
Figure 3:
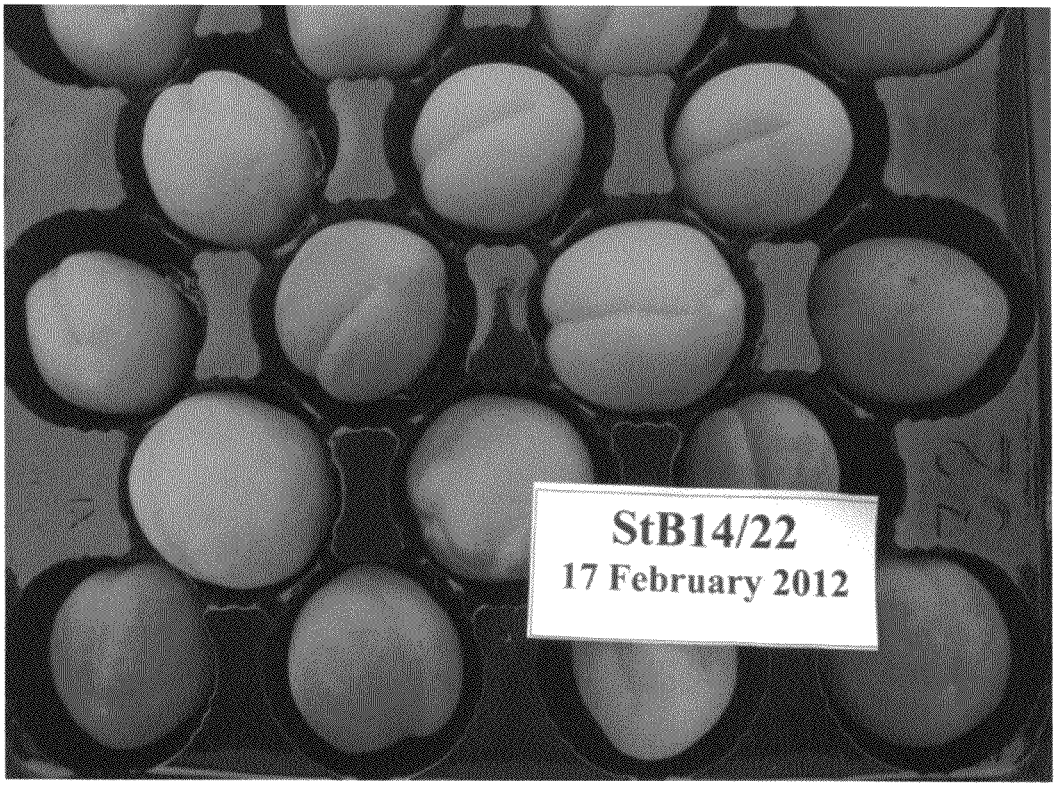
FIG. 3 shows 'StB14/22' fruit in a tray.
Figure 4:
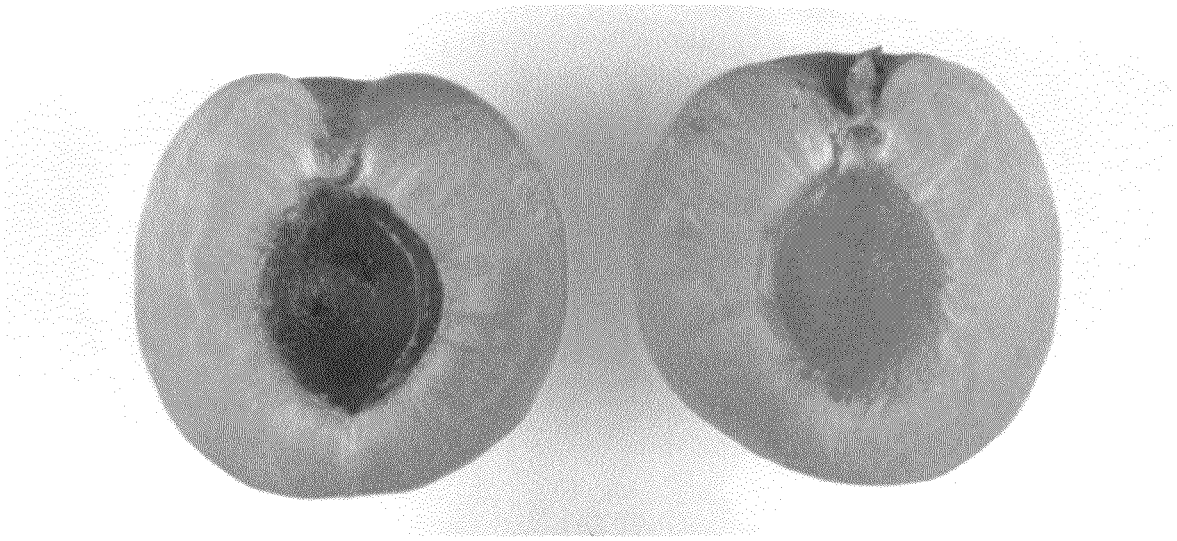
FIG. 4 shows a longitudinal section of 'StB14/22' fruit.
Figure 5:
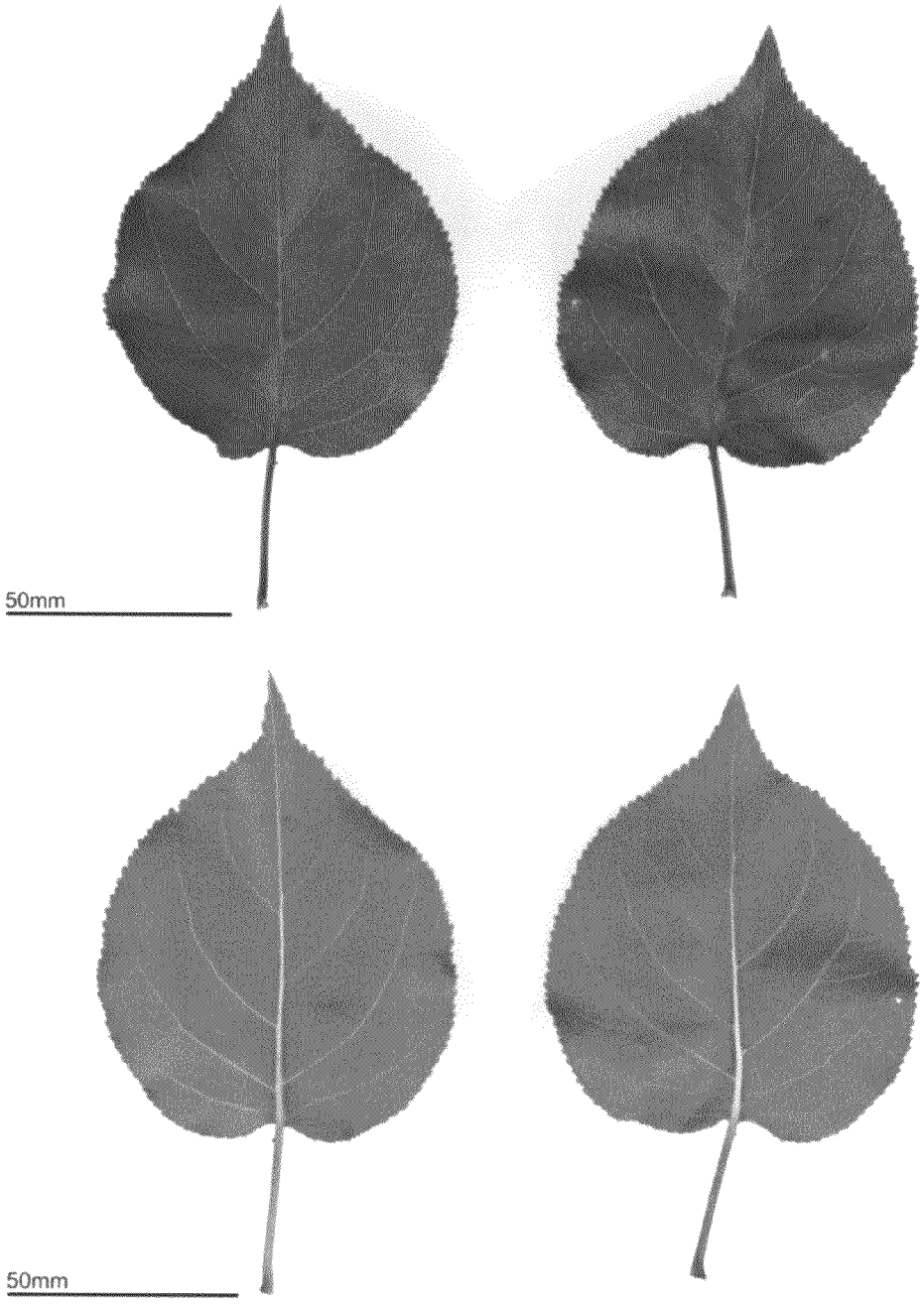
FIG. 5 shows upper (top) and underside (bottom) of 'StB14/22' leaves.

The following is a brief description of the new variety with color terminology in accordance with The Royal Horticultural Society Colour Charts (R.H.S.C.C) 2001 edition. The specimens described were grown at Clyde, New Zealand. The observations were made over the 2012-2013 seasons on 7 year old mature trees.

Tree: Average of approximately 3.5 m tall with a spread of approximately 2.3 m, medium vigour with an upright to spreading habit 'StB14/22' scions are compatible on peach seedlings ('Golden Queen') root stocks. Tree health is considered to be good under Central Otago conditions in New Zealand with a medium level of precocity compared to commercially grown varieties under similar conditions.

Trunk: Average circumference of a mature trunk, approximately 30 cm from the graft union was 365 mm. Trunk color was observed to be near brown N200B, with a reticulate bark texture, and a medium density distribution of near greyed orange 165D oblanceolate lenticels which averaged approximately 3.5 mm long and 2.0 mm wide.

One-year-old shoot: Observed in winter were observed to be near greyed orange 166A in color with near greyed-orange 166A, medium sized bud supports which averaged approximately 4.0 mm in diameter and 4.4 mm in height. Dormant buds were observed to be near greyed orange 166A in color and approximately 3.4 mm long and 1.9 mm wide.

Leaves: The leaves examined were fully expanded and harvested from the central third of growing shoots in summer. The overall shape of the leaves was observed to be broad ovate with an acute acuminate tip approximately 15.7 mm long, a truncate base and serrate margins with a weak undulation. Leaves are arranged alternatively and averaged 96.6 mm long and 81.7 mm wide. The color of the upperside was near green 137A and the underside near green 137C. The leaf had a slight gloss and the profile in cross section was moderately concave. The venation pattern of the leaf was reticulate and the color of the venation near yellow green 145C.

Petiole: The average petiole length of fully expanded leaves was 41.5 mm and 1.7 mm in diameter. The upperside of the petioles had a medium anthocyanin coloration of near greyed purple 187C. Petioles were observed to have between two and three small nectaries close to the leaf base which had an average diameter of 0.9 mm.

Flowers: Observations were made at full bloom unless otherwise stated. Bud burst was recorded in early September (approximately $6^{th}$ September), with full bloom occurring mid September (approximately $12^{th}$ September). Flowers were medium sized, the average diameter of an open flower with petals pressed flat was 31 mm and distributed approximately equally on spurs and one-year-old shoots, with a medium strength fragrance.

Corolla: Five petals per flower, with an average length of 11 mm (excluding claw) and an average width of 13 mm and a 0.5 mm claw. The petal shape (excluding claw) was approximately circular with a smooth but sinuate margin. Petals were near white, N155D, at full bloom with near red-purple 62B veins.

Stamens: An average of around 24 per flower. Filaments were translucent white in color with near yellow-orange 17D anthers and near greyed-orange 163B pollen. Anthers were on average 1.2 mm long and 1.0 mm wide.

Carpel: Pistals were on average approximately 17 mm and colored near yellow-green 154D. The stigma sat above the anthers.

Pedicel: Average approximately 5.2 mm long and 6.8 mm wide.

Calyx: Five sepals per flower, average length of 7.0 mm and width 4.5 mm with a right angle apex and a smooth margin. Colored near red purple 59B.

Fruit: Fruit at horticultural maturity were medium sized and observed to be on average 70-100 g, with an average height of 48.9 mm, average lateral width of 49.1 mm, and average ventral width of 44.9 mm. 'StB14/22' fruit were slightly asymmetric and were circular in lateral view and ovate in ventral view with a slightly sunken suture and a truncate apex. The stalk cavity was shallow, approximately 2.9 mm deep. The skin surface was smooth with minimal pubescence, medium gloss, a background color of near orange 25B, and approximately 25-40% overcolor colored near red 46B made up of a combination of a solid flush and isolated spots. The flesh color was near orange 25A and near orange 25B in the stone cavity with no whiteness around the stone. The flesh texture was fine and firm, an average of approximately 2.9 kgf, with a very weak adherence to the stone and average soluble solids of approximately 18.8%.

Stone: Observations were made on dry stones unless otherwise stated. Stones were elliptic in shape, lateral view, with an acute apex, and obtuse base. Stones were on average approximately 3.7 g, 28.9 mm long, with an average lateral width of 22.4 mm, and an average ventral width of 13.3 mm. The stone was colored near grey brown N199D.

Harvest timing: Fruit begin ripening late in the season, approximately $17^{th}$-$19^{th}$ February in Clyde, New Zealand.

Use: Fresh eating.

Keeping quality: Has been shown to store very well for at least four weeks at 0° C.

Pest and disease: 'StB14/22' has no known particular tolerances or susceptibilities to pests and diseases associated with apricot trees.

The invention claimed is:

1. A new and distinct apricot plant substantially as herein illustrated and described.

* * * * *